US012595503B2

(12) United States Patent
Sparbier

(10) Patent No.: US 12,595,503 B2
(45) Date of Patent: Apr. 7, 2026

(54) REFERENCE DATASET-BASED, SPECTROMETRIC CHARACTERIZATION OF CELL SUBSTRATES USING SUB-LIBRARIES

(71) Applicant: Bruker Daltonics GmbH & Co. KG, Bremen (DE)

(72) Inventor: Katrin Sparbier, Bremen (DE)

( * ) Notice: Subject to any disclaimer, the term of this patent is extended or adjusted under 35 U.S.C. 154(b) by 575 days.

(21) Appl. No.: 18/056,107

(22) Filed: Nov. 16, 2022

(65) Prior Publication Data

US 2023/0159977 A1 May 25, 2023

(30) Foreign Application Priority Data

Nov. 19, 2021 (DE) .............................. 102021130356

(51) Int. Cl.
| | | |
|---|---|---|
| *C12Q 1/18* | (2006.01) | |
| *G01N 33/68* | (2006.01) | |
| *G16B 20/00* | (2019.01) | |
| *G16B 40/10* | (2019.01) | |

(52) U.S. Cl.
CPC ........... *C12Q 1/18* (2013.01); *G01N 33/6851* (2013.01); *G16B 20/00* (2019.02); *G16B 40/10* (2019.02)

(58) Field of Classification Search
None
See application file for complete search history.

(56) References Cited

U.S. PATENT DOCUMENTS

| | | | |
|---|---|---|---|
| 2002/0138210 A1 | 9/2002 | Wilkes et al. | |
| 2008/0009029 A1 | 1/2008 | Govorun et al. | |
| 2011/0012016 A1 | 1/2011 | Maier et al. | |
| 2011/0202282 A1 | 8/2011 | Kostrzewa | |
| 2014/0335556 A1 | 11/2014 | Franzen et al. | |
| 2020/0291446 A1 | 9/2020 | Becker et al. | |

FOREIGN PATENT DOCUMENTS

| | | |
|---|---|---|
| CN | 113574373 | 10/2021 |
| DE | 112005001530 T5 | 5/2007 |
| DE | 102006021493 A1 | 4/2010 |
| DE | 102009032649 A1 | 1/2011 |
| DE | 102010006450 A1 | 8/2011 |
| DE | 102010023452 A1 | 12/2011 |
| DE | 102013022016 A1 | 6/2015 |
| EP | 2806275 A1 | 11/2014 |
| EP | 2801825 A1 | 11/2015 |
| WO | 2006002537 A1 | 1/2006 |
| WO | 2011154517 A1 | 12/2011 |
| WO | 2014187517 A1 | 11/2014 |
| WO | 2015090727 A1 | 6/2015 |
| WO | 2017069935 A1 | 4/2017 |
| WO | 2018099500 A1 | 6/2018 |

OTHER PUBLICATIONS

Fenselau, et al., "Characterization of Intact Microorganisms by Maldi Mass Spectrometry", Mass Spectrometry Reviews, 2001, 20, pp. 157-171.
Naumann, D. "Infrared Spectroscopy in Microbiology", Encyclopedia of Analytical Chemistry, pp. 102-131, (2000).
Idelevich et al., "Rapid detection of antibiotic resistance by MALDI-TOF mass spectrometry using a novel direct-on-target microdroplet growth assay", Clinical Microbiology and Infection 24 (2018) pp. 738-743.
Idelevich et al., "Rapid Direct Susceptibility Testing from Positive Blood Cultures by the Matrix-Assisted Laser Desorption Ionization-Time of Flight Mass Spectrometry-Based Direct-on-Target Microdroplet Growth Assay", Journal of Clinical Microbiology, Oct. 2018 vol. 56 Issue 10 pp. 913-918.
Nix et al., "Methicillin Resistance Detection by MALDI-TOF MS", Frontiers in Microbiology, vol. 11, Article 232 (2020).
Li et al., "Rapid antimicrobial susceptibility testing by matrix-assisted laser desorption ionization-time of flight mass spectrometry using a qualitative method in Acinetobacter baumannii complex", Journal of Microbiological Methods 153 (2018) pp. 60-65.
Neonakis et al., "Detection of carbapenemase producers by matrix-assisted laser desorption-ionization time-of-flight mass spectrometry (MALDI-TOF MS)", European Journal of Clinical Microbiology & Infectious Diseases (2019), https://doi.org/10.1007/s10096-019-03620-0.
Horseman et al., Rapid qualitative antibiotic resistance characterization using VITEK MS, Diagnostic Microbiology and Infectious Disease vol. 97, Issue 4, (2020), 115093.
Idelvich, "Matrix-Assisted Laser Desorption Ionization-Time of Flight Mass Spectrometry for Antimicrobial Susceptibility Testing", J. Clin. Microbiol., 59, 12 (2021).
Nomura, Fumio et al., "Proteome-based bacterial identification using matrix-assisted laser desorption ionization—time of flight mass spectrometry (MALDI-TOF MS) : A revolutionary shift in clinical diagnostic microbiology", Biochimica Et Biophysica Acta (BBA), Proteins & Proteomics, Elsevier, Netherlands, V. 1854, N. 6, 2014.

*Primary Examiner* — Michelle F. Paguio Frising
(74) *Attorney, Agent, or Firm* — DECODE Legal Inc.

(57) ABSTRACT

The invention relates to methods for spectrometric characterization of a test cell substrate. The characterization comprises taxonomic classification and determination of a property of interest of the test cell substrate. The characterization may be based on mass-spectrometric measurement data. The property of interest may be a resistance or susceptibility to a growth-influencing factor. After comparing first spectrometric measurement data of the test cell substrate with a provided reference library, a sub-library is created comprising those reference datasets from the reference library that are classified as allowing a taxonomic classification of the test cell substrate. Second spectrometric measurement data after a second preparation of the test cell substrate under conditions that serve to determine a property of interest of the test cell substrate is compared with the sub-library and allow a reliable determination of the property of interest.

15 Claims, 4 Drawing Sheets

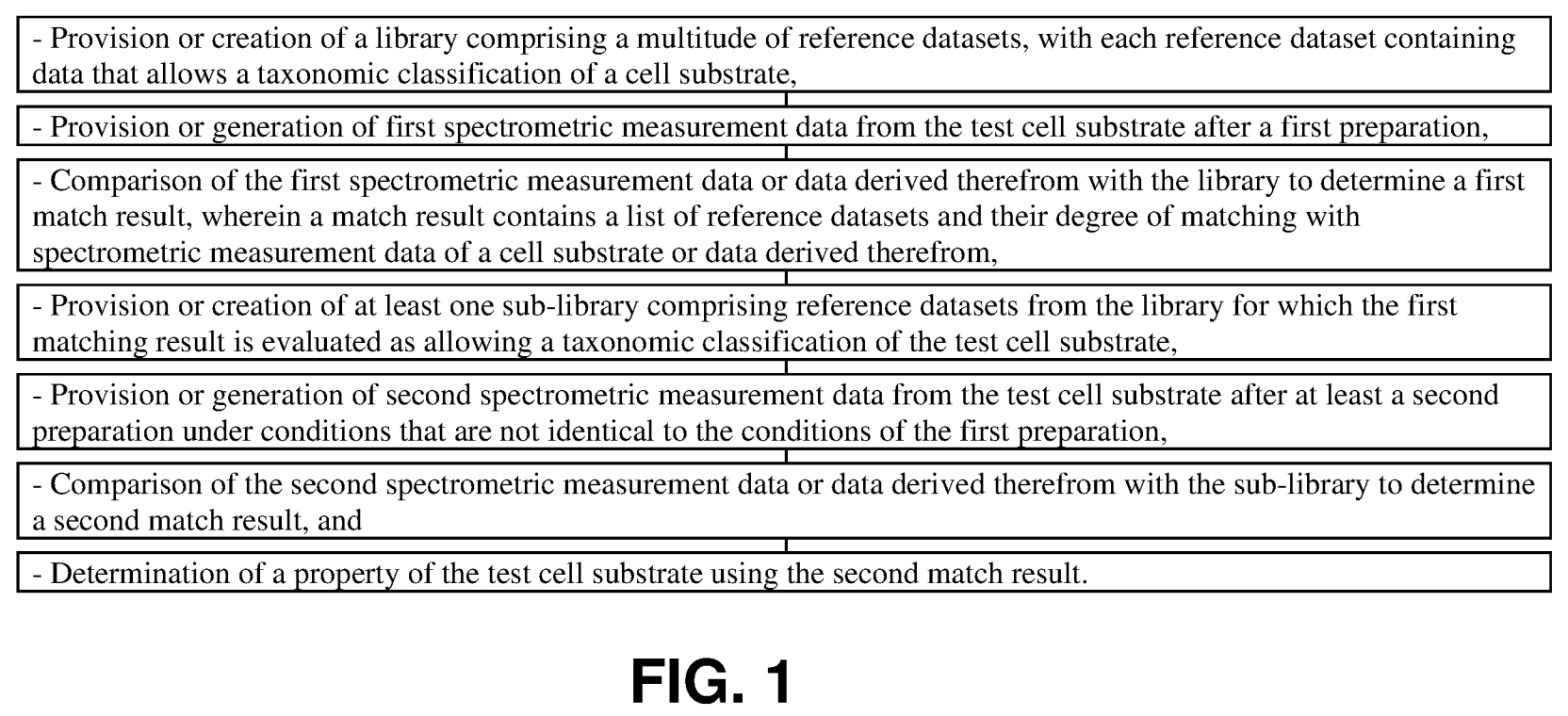

- Provision or creation of a library comprising a multitude of reference datasets, with each reference dataset containing data that allows a taxonomic classification of a cell substrate,

- Provision or generation of first spectrometric measurement data from the test cell substrate after a first preparation,

- Comparison of the first spectrometric measurement data or data derived therefrom with the library to determine a first match result, wherein a match result contains a list of reference datasets and their degree of matching with spectrometric measurement data of a cell substrate or data derived therefrom,

- Provision or creation of at least one sub-library comprising reference datasets from the library for which the first matching result is evaluated as allowing a taxonomic classification of the test cell substrate,

- Provision or generation of second spectrometric measurement data from the test cell substrate after at least a second preparation under conditions that are not identical to the conditions of the first preparation,

- Comparison of the second spectrometric measurement data or data derived therefrom with the sub-library to determine a second match result, and

- Determination of a property of the test cell substrate using the second match result.

FIG. 1

REFERENCE DATASET-BASED,
SPECTROMETRIC CHARACTERIZATION
OF CELL SUBSTRATES USING
SUB-LIBRARIES

BACKGROUND OF THE INVENTION

Field of the Invention

The invention relates to a method for spectrometric char-
acterization of properties of interest of cell substrates with
generation of measurement dataset-based sub-libraries from
a provided library, which contains reference datasets suit-
able for taxonomic classification of the cell substrate,
wherein, in order to determine the property of the test cell
substrate, spectrometric measurement data is compared with
the library and at least one sub-library is generated there-
from.

Description of the Related Art

The Prior Art is explained hereinafter with reference to a
special aspect. However, this should not be construed as a
limitation of the invention disclosed below. Useful further
developments and modifications of what is known from the
Prior Art may also be applicable beyond the comparatively
narrow scope of this introduction and will become readily
apparent to skilled practitioners in the field after reading the
disclosure of the invention following this introduction.

Characterizing microorganisms spectrometrically and
classifying them taxonomically is a well-known technique.
One example is a mass time-of-flight (TOF) analysis using
ionization by matrix-assisted laser desorption/ionization
(MALDI), see the review article by Fenselau and Demirev,
*Characterization of Intact Microorganisms by Maldi Mass
Spectrometry*, Mass Spectrometry Reviews, 2001, 20, 157-
171. For many microorganisms such as bacteria and fungi,
this method provides reliable results on a taxonomic level
down to the genus or species without any prior knowledge,
essentially based on the mass signature of ribosomal pro-
teins. Commercial systems are supplied by, for example,
Bruker, MALDI Biotyper®, and bioMérieux, Vitek® MS.

Generally, the underlying characterization algorithms are
often based on comparisons of information derived from
measured mass spectra, e.g., peak lists, with reference data
from a library or database, and have been developed over
time in a variety of ways. For example, patent publication
DE 10 2009 032 649 A1 (corresponding to GB 2 471 746 A
and US 2011/0012016 A1) explains a two-step identification
procedure that can identify microbes at the species or
subspecies level, even if they have very similar reference
spectra. Patent publication DE 10 2010 006 450 A1 (corre-
sponding to US 2011/0202282 A1 and EP 2 354 796 A1)
also relates to the identification of microbes in a sample by
calculating the similarities between a mass spectrum of the
sample and reference spectra in large spectral libraries, using
a multistage method.

Patent publication WO 2017/069935 A1 relates to a
method for identifying microorganisms by MALDI-TOF
mass spectrometry, consisting in acquiring a MALDI mass
spectrum of a microorganism, detecting peaks in the
acquired MALDI spectrum, generating a peak list compris-
ing the mass and intensity of the detected peaks in the
spectrum, acquiring a database of protein sequences derived
from DNA sequences, generating a sub-database of ribo-
somal proteins from the protein sequences and their masses
in the database, comparing the masses of the detected peaks in the acquired MALDI spectrum with the masses of ribo-
somal proteins in the generated sub-database, evaluating the
matches obtained above for each represented microorgan-
ism, generating a peak list of the exact masses of the
matching ribosomal proteins, recalibrating the peak list,
which comprises mass and intensity, with the peak list of the
exact masses of the matching ribosomal proteins, identifying
a microorganism with the highest score, and repeating until
a desired improvement in the recalibrated peak list or a
validated identification is achieved.

Another example of spectrometric characterization of
microorganisms is absorption spectrometric analysis using
infrared light. See, for example, the monograph of Dieter
Naumann: *Infrared Spectroscopy in Microbiology*, Encyclo-
pedia of Analytical Chemistry, pp. 102-131, 2000. This
method has proven particularly useful for subtyping below
the taxonomic level of the species, with appropriate prior
knowledge of the species of the microorganism, which can
be obtained, for example, by mass-spectrometric analysis
(DE 10 2013 022 016 A1, corresponding to WO 2015/
090727 A1). An example of a commercially available sys-
tem in this field is IR Biotyper® from Bruker.

Here too, there have been further developments. For
example, patent publication DE 11 2005 001 530 T5 (cor-
responding to WO 2006/002537 A1) describes a method for
the identification of microorganisms that comprises obtain-
ing at least one spectral image of the microorganism with
multiple pixels and selecting one or more spectra from the
spectral image with multiple pixels on the basis of prede-
termined spectral properties, wherein the selected spectra
comprise spectral information properties of the microorgan-
ism.

Furthermore, it is known that other properties of a micro-
organism can be characterized spectrometrically, in particu-
lar their susceptibility or resistance to a bioactive substance,
e.g., an antimicrobial agent such as an antibiotic or antimy-
cotic. Phenotypic or cell-based approaches are based on
detecting microorganism growth, or its absence, in the
presence of a bioactive substance, with reliable taxonomic
assignment of the species playing an important role (DE 10
2006 021 493 A1, corresponding to GB 2 438 066 A and US
2008/0009029 A1).

Other approaches, in contrast, can be substance-specific
and detect any changes in the bioactive substance or the
surrounding incubation environment caused by co-incuba-
tion of the microorganism. An example of this is the
hydrolysis of a β-lactam antibiotic by a β-lactamase secret-
ing microorganism (DE 10 2010 023 452 A1, corresponding
to WO 2011/154517 A1) or the degree of metabolism of a
nutrient, which may be isotopically labeled, by the micro-
organism (EP 2 801 825 A1, corresponding to US 2014/
0335556 A1 or DE 10 2014 000 646 A1, corresponding to
WO 2015/107054 A1).

Another approach is disclosed in patent publication EP 2
806 275 A1 (corresponding to WO 2014/187517 A1). A
mass-spectrometric method for determining microbial resis-
tance to antibiotics involves culturing microbes in an anti-
biotic-amended medium also containing a reference sub-
stance added in a measured amount, and recording mass
spectra of the microbes, including the reference substance
after culturing, and then evaluating the growth on the basis
of the signals from the reference substance in the mass
spectra.

Patent publication WO 2018/099500 A1 explains meth-
ods for the preparation of living, microbial samples and
microorganisms for subsequent mass-spectrometric measurement and evaluation. The preparation can take place directly on a mass-spectrometric sample support.

Other notable publications include: E. A. Idelevich et al., *Rapid detection of antibiotic resistance by MALDI-TOF mass spectrometry using a novel direct-on-target microdroplet growth assay*, Clinical Microbiology and Infection 24 (2018) 738-743; M. Li et al., *Rapid antimicrobial susceptibility testing by matrix-assisted laser desorption ionization-time of flight mass spectrometry using a qualitative method in Acinetobacter baumannii complex*, Journal of Microbiological Methods 153 (2018) 60-65; Idelevich et al., *Rapid Direct Susceptibility Testing from Positive Blood Cultures by the Matrix-Assisted Laser Desorption Ionization-Time of Flight Mass Spectrometry-Based Direct-on-Target Microdroplet Growth Assay*, Journal of Clinical Microbiology, October 2018 Volume 56 Issue 10 e00913-18; loannis K. Neonakis et al., *Detection of carbapenemase producers by matrix-assisted laser desorption-ionization time-of-flight mass spectrometry* (MALDI-TOF MS), European Journal of Clinical Microbiology & Infectious Diseases 2019, https://doi.org/10.1007/s10096-019-03620-0; Nix et al., *Methicillin Resistance Detection by MALDI-TOF MS*, Frontiers in Microbiology, 1 Feb. 2020, Volume 11, Article 232; and Timothy S. Horseman et al., *Rapid qualitative antibiotic resistance characterization using VITEK MS*, Diagnostic Microbiology and Infectious Disease Volume 97, Issue 4, August 2020, 115093.

For this reason, there is a need for an improved method for spectrometric characterization of cell substrates of interest and, in particular, microorganisms of interest. Further objectives that can be achieved by the invention will be immediately apparent to the person skilled in the art from reading the disclosure below.

SUMMARY OF THE INVENTION

The invention relates to methods for spectrometric characterization of a test cell substrate, such as a test microorganism. The characterization may be based on mass-spectrometric measurement data. The invention is based on the knowledge that a library containing reference datasets that enable a taxonomic classification of the test cell substrate can be used in such a way that, after a first successful taxonomic classification of a cell substrate being tested, i.e., after a first comparison of the measurement data with the reference datasets in the library and sufficient similarity between the measurement data and at least one reference dataset from the library, thereby enabling a taxonomic classification, it is then possible to create sub-libraries with which further spectrometric measurement data of the same cell substrate from at least one further experimental preparation can be compared. In particular, sub-libraries can be used which comprise spectrometric reference datasets that have been evaluated as allowing a taxonomic classification of the test cell substrate in a first match result of the spectrometric measurement data of the test cell substrate. The use of such sub-libraries for spectrometric characterization of a test cell substrate improves the specificity of the taxonomic classification of the test cell substrate in the further preparations and the determination of properties of the test cell substrate identified by means of the experimental preparations, since the reliable taxonomic classification of a test cell substrate plays an important role for determining properties based on spectrometric measurement data.

The first match result makes it possible, for example, to use the library to derive sub-libraries comprising reference datasets that are similar to the spectrometric measurement result of the cell substrate, i.e., which have a sufficiently high degree of matching to enable a taxonomic classification of the cell substrate by matching, or which are dissimilar to the spectrometric measurement result, i.e., are not a sufficiently good match with the spectrometric measurement data to enable a taxonomic classification, in particular of the species or genus.

A first sub-library comprising reference datasets from the library with a high degree of matching with the spectrometric measurement data, which are evaluated as allowing a taxonomic classification, can be used for that purpose and for determining properties of the same test cell substrate, if the test cell substrate is prepared under conditions that differ from those of the first preparation. In this case, the spectrometric measurement data of the test cell substrate from the further preparation is compared with the reference datasets from the first sub-library in at least one further match result. This improves the specificity of the taxonomic classification on the basis of this further match result, which in turn has a positive effect on the spectrometric determination of a property of the test cell substrate that is determined by the conditions of the further preparation not being identical to those of the first preparation.

Furthermore, it was recognized that after a first successful taxonomic classification, further sub-libraries can be created from the provided library, in addition to a first sub-library, and used to improve the results of the taxonomic classification of the test cell substrate and/or the determination of properties of the test cell substrate using further preparations. One example of this is a second sub-library, which comprises only reference datasets that are evaluated as not allowing a taxonomic classification, especially of the species or genus of the cell substrate, based on the first spectrometric measurement data. This second sub-library can be used as a negative control, because a match result between the spectrometric measurement results of the test cell substrate from a further preparation and the spectrometric reference datasets of the second sub-library that is evaluated as allowing a taxonomic classification (e.g., of the genus or species) is not to be expected and should even be excluded. Reference datasets that, in the first match result, are considered to be dissimilar or are evaluated as not permitting a taxonomic classification, in particular of the species or genus, can consequently play an important role in the analysis and evaluation of the spectrometric measurement data from further preparations, since a taxonomic classification or determination of properties for a taxonomic classification of the test cell substrate that differs from the first match result can be an indication of impurity or contamination of the sample or the presence of an inhomogeneity in the test cell substrate itself.

By the provision or generation of reference datasets, specific to a cell substrate and selected depending on a first match result of the spectrometric measurement data with a comprehensive, general library, in at least one sub-library that is used for matching in further spectrometric analyses of the same test cell substrate, the specificity of the taxonomic classification of the test cell substrate prepared under changed conditions (e.g., cultured) and the determination of test cell substrate properties can be further improved.

The method comprises: The provision or creation of a library comprising a multitude of reference datasets, with each reference dataset containing data that allows a taxonomic classification of a cell substrate. In particular, the library comprises reference datasets that are specific to a spectrometric detection method used and differ from reference datasets of other spectrometric detection methods such that they are incompatible with each other. Reference data sets may comprise spectrometric measurement data, or data derived therefrom, obtained from known cell substrates and, in particular, microorganisms. An exemplary library comprises reference datasets of spectrometric detection methods of microorganisms, such as reference datasets of mass-spectrometric detection methods of Enterobacteriaceae, which might, for example, be generated using a validated MALDI time-of-flight system, e.g., the MALDI Biotyper® (Bruker).

A reference dataset may comprise a spectrum or a data n-tuple derived from a spectrum. One example of a data n-tuple is a list of frequency (abundance) information in the spectral signal and narrow mass channels associated with it, plus any meta-information about the spectrum, if applicable. Another example of a data n-tuple is a list of absorption information in the spectral signal and associated narrow wave number channels, plus any meta-information about the spectrum if applicable. Derived data can contain, for example, peak lists of the most prominent spectral signals generated from the original spectra or otherwise reduced data, for example by means of baseline subtraction, derivation, noise removal and the like.

The method also comprises: provision or generation of first spectrometric measurement data from the test cell substrate after a first preparation. A preparation is a procedure by which the initially available biomass of the test cell substrate under investigation is processed and prepared for spectrometric measurement. The provision or generation of first spectrometric measurement data may comprise a repeated spectrometric measurement of the test cell substrate after a first preparation, where the measurement may be repeated 1, 2, 3, 4 or 5 times. For the provision or generation of the first spectrometric measurement data, the median of the measurements or another suitable statistical position parameter is then typically determined and used. These repetitions may have been created using biological replicates of the test cell substrate and/or technical replicates from the same preparation. The first preparation may include a multiplication step of the test cell substrate to increase the available biomass and thus enhance the detectable spectral signals compared to ubiquitous background or noise in spectrometric measurement data. The provision or generation of spectrometric measurement data may involve mass-spectrometric analysis, for example using desorbing ionization of biomass of the test cell substrate after preparation, further followed by mass-dispersive analysis of the generated ions, in particular MALDI time-of-flight (MALDI-TOF) analysis. The first preparation can be performed directly on a sample support that serves as a substrate for the provision or generation of spectrometric measurement data, e.g., a MALDI sample support such as AnchorChip™ (Bruker) or MBT Biotarget™ (Bruker) for mass-spectrometric measurements or a glass or ceramic specimen slide.

The method also comprises: comparing the first spectrometric measurement data or data derived therefrom with the library to determine a first match result, wherein a match result contains a list of reference datasets and their degree of matching with spectrometric measurement data of a test cell substrate or data derived therefrom. Examples of match results include lists of similarity scores used by commercial systems such as MALDI Biotyper® (Bruker). The logarithm of these similarity measures ("log(score)") falls into the ranges of (i) 2.0 or greater, which according to the vendor is considered a reliable determination of the species of the test cell substrate under investigation, (ii) less than 2.0 but not less than 1.7, which is considered a reliable determination of the genus of the test cell substrate under study, and (iii) less than 1.7, which is considered a failed determination. The MALDI Biotyper® System can also be used to make taxonomic classifications at other taxonomic levels such as subspecies. The range (i) can be further differentiated to reliably determine the subspecies. Other providers use similar classifications.

The method also comprises: The provision or creation of a sub-library comprising reference datasets from the library for which the first match result is evaluated as allowing a taxonomic classification of the test cell substrate. The taxonomic classification may comprise assignment of a taxon to the test cell substrate selected from the group: genus, species, subspecies and variety or serotype. The taxonomic classification may comprise assignment of a taxon to the test cell substrate selected from the group genus and/or species. The taxonomic classification of a subspecies, variety or serotype may be of interest if the variety or serotype has another property of interest, such as a different pathogenicity or resistance/susceptibility. It can be arranged that a sub-library contains only the reference dataset, from the library, which has the highest similarity measure in the first match result, i.e., the reference dataset that has the highest degree of matching with the spectrometric measurement data or data derived therefrom from the first preparation of the cell substrate (and is evaluated as allowing a taxonomic classification). It can be arranged that a sub-library comprises a certain number of reference datasets that have shown the highest degree of matching in the first match result (and are evaluated as allowing a taxonomic classification). For example, this could be the top five or top three reference datasets, although a different number (typically between one and ten) could also be used. It can be arranged that the reference datasets for which the first match result is evaluated not to allow taxonomic classification of the test cell substrate are excluded in the provision or creation of a sub-library.

It can be arranged that, after comparing the first spectrometric measurement data with the library and before providing or creating a sub-library, the degree of matching, in terms of the similarity measure and/or the logarithm of the similarity measure, between spectrometric measurement data and reference datasets that is necessary in order to be evaluated as allowing a taxonomic classification is adjusted. It can be arranged that the degree of matching between spectrometric measurement data and the library that is necessary in order to be evaluated as allowing a taxonomic classification is adjusted and/or the degree of matching between spectrometric measurement data and a sub-library that is necessary to be evaluated as allowing a taxonomic classification is adjusted. An increase in the necessary degree of matching can be provided, for example, if the first match result is evaluated as allowing a taxonomic classification into different genera, e.g., *Citrobacter* sp. and *Escherichia* sp. In such a case, the reliability of a taxonomic classification based on the first match result can be improved by adjusting the necessary degree of matching. A reduction in the necessary degree of matching can be provided, for example, if the first match result does not contain any similarity measures that are evaluated as allowing a taxonomic classification, such as a taxonomic classification of the species, but contains similarity measures that are evaluated as not allowing a taxonomic classification of the species or the genus. In these cases, such as when using the MALDI Biotyper® (Bruker), the evaluation ranges into which the logarithms of the similarity measures fall, and on the basis of which an evaluation of the match results as allowing taxonomic classification or not allowing taxonomic classification is made, can be adjusted.

In the case of the MALDI Biotyper® system, an adjustment can be made for ranges (i), (ii), and (iii) together. However, it is also possible to adjust only range (i), only ranges (i) and (ii), or ranges (ii) and (iii). Range (i) can be adjusted to a value greater than or equal to a value between 2.5 and 1.0 to provide a reliable determination of species, according to the supplier. Similarly, range (ii) can be adjusted to a value less than a value between 2.5 and 1.0 and greater than or equal to a value between 0.7 and 2.2 to allow reliable genus determination, according to the supplier. Similarly, range (iii) can be adjusted to a value less than a value between 0.7 and 2.2 in order to be evaluated as a failed taxonomic classification, i.e., not allowing taxonomic classification of the species or genus, according to the supplier. The values provided for range (i) adjustment are greater than the values for range (ii). The values provided for range (ii) adjustment are less than the values for range (i) and greater than the values for range (iii). The values provided for range (iii) adjustment are less than the values for range (ii) and less than the values for range (i).

In one embodiment, it can be arranged that the test cell substrate is a microorganism. The microorganism may be a bacterium, such as a bacterium from the Enterobacteriaceae family. In this embodiment, it can be arranged that the first preparation is a growth control and that for a second preparation of the test microorganism, an antimicrobial agent such as an antifungal or an antibiotic, in particular piperacillin/tazobactam (PIT), cefotaxime (CTX), ertapenem (ERT), ceftazidime/avibactam (CAA), meropenem (MER), ciproflaxicin (CIP), ceftazidime (CAZ), amikacin (AMK) and/or gentamicin (GEN), is selected as the growth-influencing factor.

In an exemplary embodiment, the test cell substrate is from the family of Enterobacteriaceae and it is ensured that the first preparation is a growth control, and that for a second preparation of the test microorganism, an antimicrobial agent such as an antifungal agent or an antibiotic, in particular piperacillin/tazobactam (PIT), cefotaxime (CTX), ertapenem (ERT), ceftazidime/avibactam (CAA), meropenem (MER), ciproflaxicin (CIP), ceftazidime (CAZ), amikacin (AMK) and/or gentamicin (GEN), of certain concentration is selected as the growth-influencing factor. In this embodiment, the reference datasets of the library and the mass-spectrometric measurement data of the preparations can be based on measurement data generated using the MALDI Biotyper® (Bruker) or another commercially available system.

In one embodiment, it can be arranged that the provided or created sub-library, comprising reference datasets from the library, for which the first match result is evaluated as allowing a taxonomic classification of the test cell substrate is a first provided or created sub-library. In addition to the first sub-library, it can be arranged that a second sub-library is provided or created, wherein a first and a second sub-library are not identical. Not identical means that a first sub-library and a second sub-library do not match in at least one aspect, such as the number of reference datasets contained and/or the identity of the reference datasets, whereas other aspects may well be identical. A second sub-library may comprise those reference datasets from the library for which the first match result is evaluated as not allowing a taxonomic classification, in particular of the species or genus of the test cell substrate. A second sub-library may consist of those reference datasets from the library for which the first match result is evaluated not to allow taxonomic classification (e.g., of the species or genus) of the test cell substrate.

A sub-library contains reference datasets that are also contained in the library. In particular, a sub-library contains a subset of the reference datasets from the library. A sub-library may contain a smaller number of reference datasets than the library. It is possible that the number of reference datasets in the first sub-library comprises less than 10%, less than 5%, less than 3%, less than 1%, less than 5√, less than 3√, or even less than 1√ of the number of reference datasets in the library. For example, if the library contains 3000 reference datasets, the maximum number of reference datasets in the sub-library may be limited to 3 in one example. A first and a second sub-library may together contain the same number of reference datasets as the library. A first and a second sub-library may together contain a lower number of reference datasets than the library. A first sub-library may contain the same number of reference datasets as a second sub-library. A first and a second sub-library may have an intersection of reference datasets, i.e., reference datasets may be contained in both a first and a second sub-library. A second sub-library may contain the same number of reference datasets as a first sub-library, or a larger or smaller number. In one embodiment, it can be arranged that a first sub-library is provided or created that contains a reference dataset of the library, in particular the reference dataset from the library for which the first match result is evaluated as allowing a taxonomic classification of the test cell substrate and whose similarity measure or logarithm of the similarity measure has the highest value in the first match result (best match).

In other embodiments, the first sub-library may comprise three or five reference datasets, wherein reference datasets from the library are included that are evaluated as allowing a taxonomic classification and whose similarity measures or logarithms of the similarity measures have the three or five highest values or the highest degree of matching in the first match result. Both the library and the sub-libraries resulting therefrom are, in particular, uniformly populated with reference datasets that are specific for a certain spectrometric, in particular a mass-spectrometric, detection method. Both the library and the sub-libraries resulting therefrom can, in particular, be uniformly populated with reference datasets by virtue of the reference datasets being obtained using spectrometric, in particular mass-spectrometric, detection methods or being obtained by derivation from spectrometric or mass-spectrometric measurement data.

The method also comprises: Provision or generation of second spectrometric measurement data from the test cell substrate after at least a second preparation under conditions that are not identical to those of the first preparation. Not identical means, in particular, that the conditions of the first preparation and the second preparation do not match in at least one aspect, whereas other aspects may well be identical. The provision or generation of second spectrometric measurement data may comprise a repeated spectrometric measurement of the test cell substrate after a first preparation. The measurement may be repeated 1, 2, 3, 4 or 5 times. Typically, the median of the measurements or other suitable statistical position parameter is then determined and used to provide second spectrometric measurement data. These repetitions may have been generated using biological replicates and/or technical replicates from the same preparation of the test cell substrate.

It can be arranged that the first preparation and the second preparation are provided or created at the same time. Likewise, it can be arranged that provision or generation of the first and second spectrometric measurement data from the test cell substrate is simultaneous. It can be arranged that the first and the second preparation are provided at the same time and the spectrometric measurement data of the first preparation and the second preparation are provided or created at the same time. It can also be arranged that the first and the second preparation are provided simultaneously and the spectrometric measurement data of the first preparation and the spectrometric measurement data of the second preparation are not provided or created at the same time, with the spectrometric measurement data of the first preparation typically being provided or created before the spectrometric measurement data of the second preparation. However, it can also be arranged that the first preparation and the second preparation are not provided at the same time, with the first preparation typically being provided before the second preparation. It can also be arranged that the first preparation and the second preparation are not provided simultaneously and the spectrometric measurement data of the first and second preparation are provided or created simultaneously, with the first preparation typically being provided before the second preparation. It can also be arranged that the first preparation and the second preparation are not provided simultaneously and the spectrometric measurement data of the first and second preparation are not provided or generated simultaneously, with the first preparation typically being provided before the second preparation and/or the spectrometric measurement data of the first preparation being provided or generated before the spectrometric measurement data of the second preparation.

Just like the first preparation, the second preparation may also comprise a multiplication step of the test cell substrate. Here, not identical can mean that the second preparation is carried out in the presence of a growth-influencing factor, e.g., a bioactive substance that negatively or positively influences the vitality and/or viability of the test cell substrate. The first preparation, on the other hand, can be carried out as a growth control without the use of a growth-influencing factor or, in any case, with a different concentration of the growth-influencing factor (dilution series) and can thus differ from the conditions of the second preparation in one aspect, but with otherwise identical multiplication conditions. Multiplication conditions may comprise: for example, the type and amount of a nutrient medium used, the period of incubation, environmental conditions such as temperature, composition of the ambient air, and humidity during incubation, and the like.

The provision or generation of spectrometric measurement data may comprise a mass-spectrometric analysis, for example using desorbing ionization of biomass of the test cell substrate after preparation, further followed by a mass dispersive time-of-flight analysis of the generated ions, in particular a MALDI time-of-flight analysis (MALDI-TOF).

Similarly to the first preparation, the second preparation can be performed directly on a sample support that serves as a substrate for the provision or generation of spectrometric measurement data, e.g., a MALDI sample support such as AnchorChip™ (Bruker) or MBT Biotarget™ (Bruker) for mass-spectrometric measurements or a glass or ceramic slide. In addition to the first preparation and the second preparation, further preparations of the test cell substrate can be carried out under conditions that are not identical to those of the first preparation and the second preparation or to each other. In this case, the measurement results of the subsequent preparations can be compared not only with a first sub-library but also with a second sub-library or additional sub-libraries. An additional, e.g., third sub-library, may comprise reference datasets of the library for which the first match result is evaluated as not allowing a taxonomic classification, in particular of the species or genus, and the second match result is evaluated as allowing a taxonomic classification. It is possible to perform first preparation, second preparation and, if necessary, further preparations on the same sample support, simultaneously if necessary. An example of this would be a test series for the reaction of a test cell substrate to different growth-influencing factors, e.g., bioactive substances, possibly at different concentrations. An example of this would be the determination of a minimum inhibitory concentration (MIC) of different antimicrobial agents for a test microorganism as a test cell substrate. Another example would be a dilution series for a bioactive compound, e.g., for determining a half-maximal inhibitory concentration ($IC_{50}$) of an antitumor factor, for primary tumor cells or tumor cell lines as a test cell substrate.

The method also comprises: Comparing the second spectrometric measurement data, or data derived therefrom, with the sub-library to determine a second match result. Moreover, it can be arranged that the second spectrometric measurement data, or data derived therefrom, is compared with a first sub-library to determine a second match result, and that the second spectrometric measurement data, or data derived therefrom, is compared with a second sub-library to determine a third match result. In one embodiment, the second sub-library may comprise those reference datasets of the first match result that are evaluated as not allowing a taxonomic classification (e.g., of the species or genus). However, the second sub-library may also consist of those reference datasets of the first match result which are evaluated as not allowing any taxonomic classification, in particular of the species or genus. A third match result can be used as an internal process control if the second sub-library comprises or consists of those reference datasets from the library for which the first match result is evaluated as not allowing a taxonomic classification in particular of the species or genus of the test cell substrate. In this embodiment, a third match result comprising or consisting only of similarity measures evaluated as not allowing a taxonomic classification, in particular of the species or genus, can confirm that a taxonomic classification of the test cell substrate of the second preparation and/or its property determination is reliable. In this embodiment, a third match result evaluated as allowing a taxonomic classification, in particular of the species or genus, can be used to identify the taxonomic classification and/or the determination of a property of interest of the test cell substrate as not reliable.

This could be the case if the test cell substrate does not represent a homogeneous population, i.e., if at least two cell populations of different taxonomic classification are present in the test cell substrate. Such a case can be found in a mixed infection, for example. In this embodiment, the method can be used to determine whether it is a property of the test cell substrate that the cell substrate is inhomogeneous and/or can allow taxonomic classification of the cell populations present in the test cell substrate. If a test cell substrate is inhomogeneous, then at least two taxonomically non-identical cell populations are present in the test cell substrate. If an inhomogeneous test cell substrate that has or consists of two mutually different cell populations is present, these may differ from each other, for example, at the taxonomic level of subspecies, species, genus or a higher taxonomic level. In particular, an inhomogeneous cell substrate in the sense of this application is present if the cell substrate comprises cell populations that differ at the taxonomic level of the species or a higher taxonomic level. Theoretically, mixed infections in which three or more mutually different cell populations are present are also conceivable, and these may then differ from each other on two or more taxonomic levels. In clinically relevant mixed infections, such as actinomycosis or amine colpitis, one microbial species A usually prepares the way for a second microbial species B, e.g., through tissue alterations, and enables a parallel infection with the second microbial species B. In this case, two cell populations are then present in the test cell substrate, one of which is classified according to the taxonomic classification of microbial species A and the other according to the taxonomic classification of microbial species B.

In one embodiment of the method disclosed herein, an inhomogeneity of the cell substrate can be detected. Here, inhomogeneity of the cell substrate can be determined when comparing the first spectrometric measurement data, or data derived therefrom, from the first preparation with the library to determine a first match result. This may be the case if the first match result contains two or more reference datasets that are evaluated as allowing a taxonomic classification of the test cell substrate, where the taxonomic classification of the reference datasets is not identical, i.e., differs on a taxonomic level such as subspecies, species or genus or a higher taxonomic level. Alternatively or additionally, inhomogeneity of the test cell substrate can be determined if, after a first match result, a first sub-library is created, comprising reference datasets from the library for which the first match result is evaluated as allowing a taxonomic classification of the test cell substrate, and a second sub-library is created comprising those reference datasets from the library for which the first match result is evaluated as not allowing a taxonomic classification, in particular of the species or genus of the test cell substrate.

Furthermore, in this embodiment, it is arranged that the second spectrometric measurement data, or data derived therefrom, is compared with the second sub-library to obtain a third match result, wherein the third match result contains reference datasets that are evaluated as allowing a taxonomic classification. In particular, in this embodiment, it can be arranged that the conditions of the second preparation are not identical to those of the first preparation in at least one aspect that allows the provision or generation of second spectrometric measurement data from the test cell substrate of a second preparation, wherein the aspect is chosen such that spectrometric measurement data of the cell population that could not be taxonomically classified according to the first match result is obtained in the second preparation. This can be done, for example, by applying a selection pressure to the cell population that was able to be taxonomically classified according to the first match result. Such selection pressure may lead to a reduction of the biomass of the cell population for which a taxonomic classification could be made on the basis of the first match result in the second preparation. This can be achieved by the second preparation comprising a growth-influencing factor that kills the cell population that was able to be taxonomically classified in the first preparation or reduces a growth of the cell population for which a taxonomic classification was able to be made on the basis of the first match result in the second preparation. In this embodiment, it can be arranged in particular that the second spectrometric measurement data and the second preparation of the test cell substrate are provided or prepared after comparing the first spectrometric measurement data with the library to determine a first match result. In this embodiment, it can be arranged that, in addition to determining an inhomogeneity of the test cell substrate, the taxonomic classifications of all cell populations contained in the inhomogeneous test cell substrate can also be determined.

In an exemplary embodiment, the method for spectrometrically characterizing a test cell substrate, wherein the test cell substrate is inhomogeneous, consists of the following steps:

provision or creation of a library comprising a multitude of reference datasets, with each reference dataset containing data that allows a taxonomic classification of a cell substrate, provision or generation of first spectrometric measurement data from the test cell substrate after a first preparation, comparison of the first spectrometric measurement data, or data derived therefrom, with the library to determine a first match result, wherein a match result contains a list of reference datasets and their degree of matching with spectrometric measurement data of a cell substrate, or data derived therefrom, provision or creation of a first sub-library comprising reference datasets from the library for which the first match result is evaluated as allowing a taxonomic classification of the test cell substrate, provision or creation of a second sub-library comprising those reference datasets from the library for which the first match result is evaluated as not allowing a taxonomic classification, in particular of the species or genus, of the test cell substrate, provision or generation of second spectrometric measurement data from the test cell substrate after at least a second preparation under conditions that are not identical to the conditions of the first preparation, comparison of the second spectrometric measurement data, or data derived therefrom, with the first sub-library to determine a second match result, comparison of the second spectrometric measurement data, or data derived therefrom, with the second sub-library to determine a third match result, and determining a property of the test cell substrate using the third match result, wherein inhomogeneity of the test cell substrate is determined as a property.

In this embodiment, particularly those reference datasets from the library for which the first match result is evaluated as allowing a taxonomic classification of the species or subspecies can be contained in the first sub-library.

In another embodiment, a third match result allowing a taxonomic classification, in particular of the species or genus, may also indicate that the same test cell substrate was not used for the first and second preparations. In this embodiment, the first and the third match results comprise reference datasets which are evaluated as allowing a taxonomic classification of the test cell substrate and the second match result comprises reference datasets which are evaluated as not allowing a taxonomic classification of the test cell substrate. In this embodiment, particularly those reference datasets from the library for which the first match result is evaluated as allowing a taxonomic classification of the species or subspecies can be contained in the first sub-library.

The method also comprises: Determination of a property of the test cell substrate using the second match result. For determining a property of the test cell substrate, determining a similarity measure or a logarithm of a similarity measure, such as a log(score), may be sufficient for the test cell substrate after a second preparation after comparing against a sub-library.

The property to be determined may comprise a susceptibility and/or resistance of the test cell substrate to a growth-influencing factor. In particular, the property to be determined may comprise a minimum inhibitory concentration (MIC) of a bioactive substance for the test cell substrate. Examples of the property to be determined include the MIC of an antimicrobial agent such as an antibiotic for a microorganism, an antifungal, or the half-maximal inhibitory concentration ($IC_{50}$) of an antitumor agent. The determination of a property of the test cell substrate, e.g., when determining a resistance/susceptibility to a growth-influencing factor, can be inferred from the log(score) of the second match result, for example. A log(score) in the second match result that is evaluated as allowing a taxonomic classification indicates a resistance, while a log(score) that is evaluated as not allowing a taxonomic classification, in particular of the species or genus, indicates a susceptibility of the test cell substrate. The method may also comprise: Determination of a property of the test cell substrate using a third match result when a first and a second sub-library are provided or created. Properties of the test cell substrate determined using a third match result may include the inhomogeneity of the test cell substrate or the fact that the same test cell substrate was not used for the first and second preparations, for instance, due to intervening impurity or contamination.

The present disclosure addresses the need to provide an improved method for spectrometric characterization of cell substrates and, in particular, microorganisms. This characterization includes their taxonomic classification and the determination of properties of the cell substrate. In particular, the method improves the specificity of a spectrometric taxonomic classification and the determination of a property of cell substrates and, in particular, improves the specificity of the taxonomic classification of cell substrates, particularly microorganisms, by reducing second comparison results that are false-positively evaluated as allowing a taxonomic classification, for example. In time-critical scenarios, such as clinical microbial diagnostics, the method enables faster provision of a reliable, i.e., highly specific, determination of critical properties of test cell substrates, particularly test microorganisms, such as susceptibility and/or resistance to certain growth-influencing factors, e.g., antibiotics or antimycotics. This enables faster treatment of patients through improved quality assurance because possible time-consuming downstream procedures to determine individual cell substrate properties of interest are no longer required.

Within the scope of the invention, it was found that comparing the spectrometric measurement result of the test cell substrate of the second preparation with the first sub-library instead of the entire library, which often contains several thousand reference datasets, can, as a second match result, increase the specificity in determining at least one property of the test cell substrate. Furthermore, within the scope of the invention, it was recognized that further spectrometric measurement results, such as mass-spectrometric measurement results, from the test cell substrate (from a biological replica, where applicable) from a second preparation can be checked against a second sub-library as an internal process control. The second sub-library may comprise reference datasets of the entire library for which the first match result is evaluated as not allowing a taxonomic classification, in particular of the species or genus. The resulting third match result allows, for example, conclusions to be drawn as to whether an error may have occurred during the preparation of the test cell substrate from the second preparation and the test cell substrate has been mixed up, or whether the test cell substrate consists of a homogeneous population or has been unintentionally contaminated between the first and second preparation.

BRIEF DESCRIPTION OF THE DRAWINGS

The invention can be better understood by referring to the following illustrations. The elements in the illustrations are not necessarily to scale, but are primarily intended to illustrate the principles of the invention (mostly schematically). In the illustrations, the same reference numbers designate corresponding elements in the different views.

FIG. 1 shows a diagram of the main procedural steps for spectrometric characterization of a test cell substrate.

DETAILED DESCRIPTION

While the invention has been illustrated and explained with reference to a number of embodiments thereof, those skilled in the art will recognize that various changes in form and detail may be made to it without departing from the scope of the technical teaching as defined in the appended claims.

FIG. 1 shows a diagram of the main procedural steps for spectrometric characterization of a test cell substrate.

Figure 2:
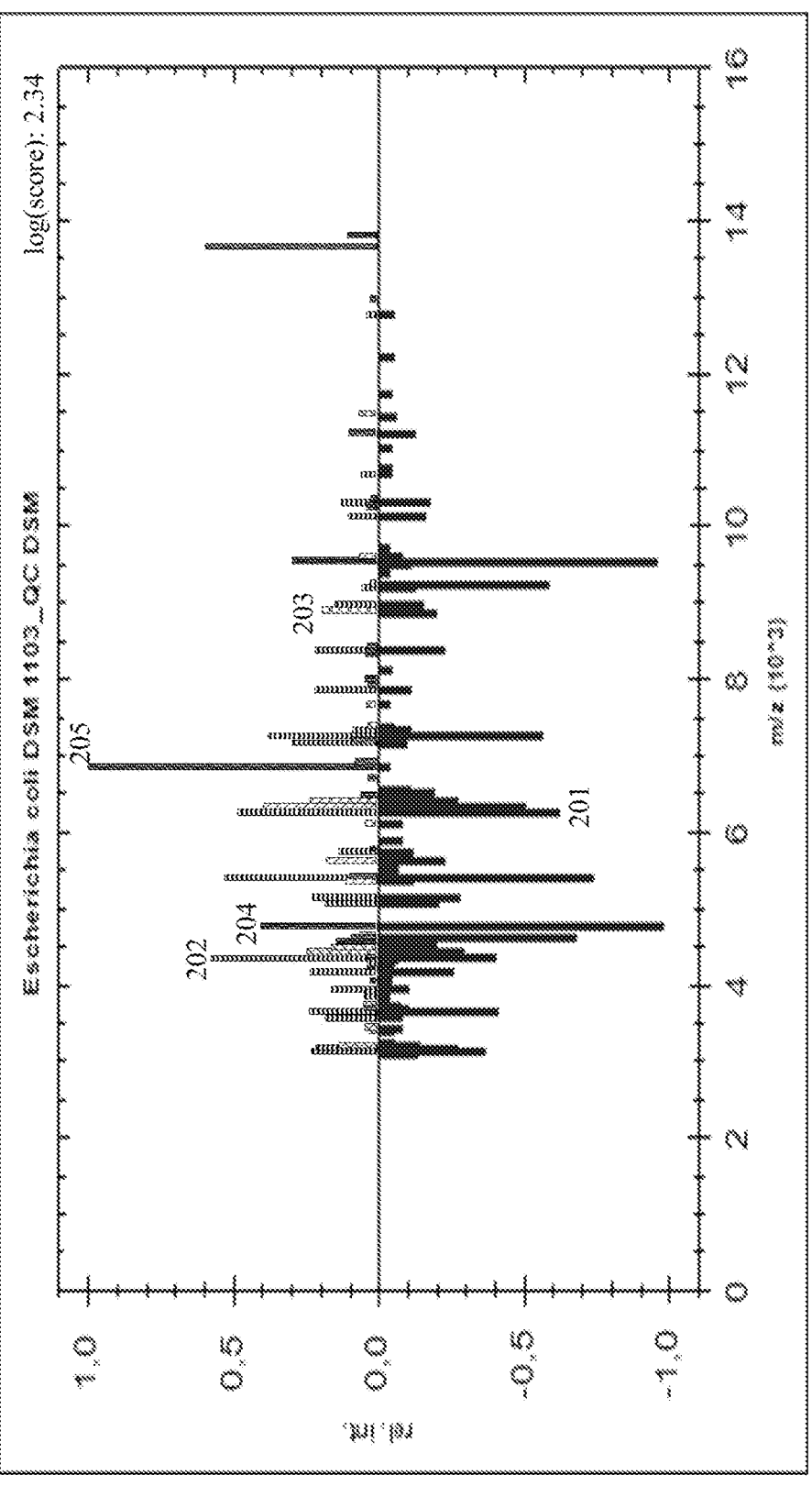
FIG. 2 shows an example of a mass-spectrometric analysis of a first preparation designed as a growth control and the comparison of the mass-spectrometric data with a relevant reference library from the MALDI Biotyper® to identify the test cell substrate E. coli. The highest degree of matching of the measured mass-spectrometric data with reference datasets selected from the library 201 was determined in terms of the logarithm of the similarity measure (log(score)) of 2.34 for a mass-spectrometric reference spectrum of E. coli. Thus, by comparing the mass spectrum with the reference library, the test cell substrate was reliably taxonomically classified as E. coli.

FIG. 2 shows a schematic linear mass spectrum of a mass-spectrometric measurement of a test cell substrate of a first preparation that was designed as a growth control. The mass spectrum of the growth control measured with the MALDI Biotyper® was compared with all the mass-spectrometric reference datasets from the provided library, which contains many thousands of reference spectra. For a reference dataset comprising a mass spectrum of *Escherichia coli*, the highest degree of matching was determined in terms of the logarithm of the similarity measure (log(score)) of 2.34. The reference peaks 201 from the reference library used to determine the degree of matching are shown as solid bars in the negative value range (butterfly graph). The degree of matching of this match result was evaluated as reliably allowing a taxonomic classification of the species because the log(score) was greater than 2.0. Those mass peaks that were able to be assigned with high reliability to a peak of the reference dataset in the match result are shown as horizontally hatched bars in the positive range of values 202, while those that could still be assigned with sufficient reliability to a peak of the reference dataset, are shown as cross-hatched bars in the positive value range 203, and those peaks that could not be sufficiently assigned to a peak of the reference dataset are shown as dotted bars in the positive value range 204. The relative quantification standard used 205 was measured but not used for taxonomic classification, so it is shown as a dotted bar.

As proof of principle for the feasibility of the disclosed procedure, a cefotaxime-susceptible *E. coli* was selected as the test cell substrate and applied to the determination of a characteristic of the microorganism under investigation using a MALDI Biotyper® system. For this purpose, the resistance/susceptibility of the test cell substrate to a growth-influencing substance, in this example the antibiotic cefotaxime (CTX), was investigated using a prior art method and the method disclosed herein.

Figure 3:
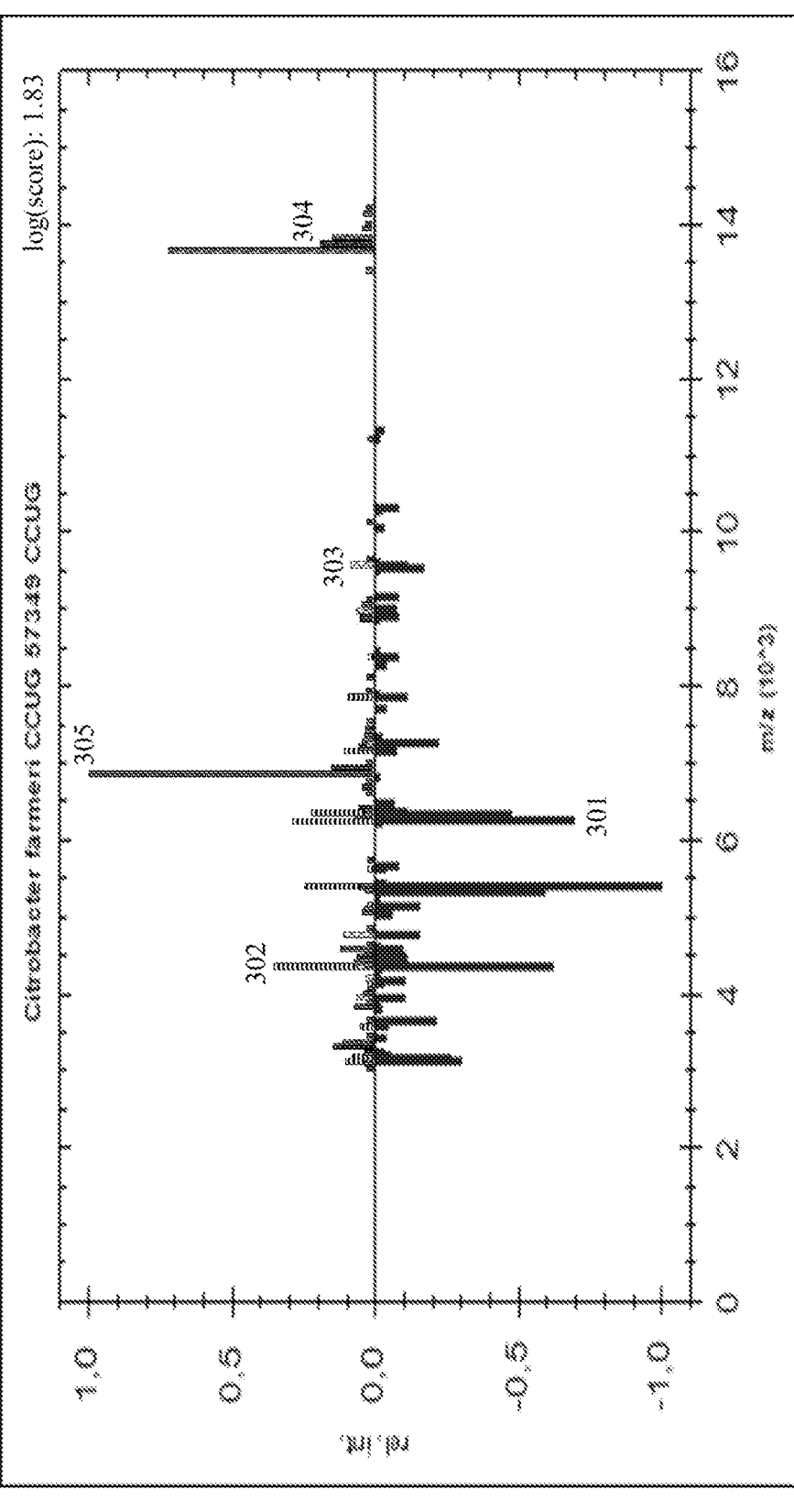
FIG. 3 shows an example of mass-spectrometric analysis of a second preparation of the same test cell substrate E. coli cultured in a cefotaxime (CTX)-containing nutrient medium ((CTX) treatment), as performed for FIG. 2. The comparison of the spectrometric measurement data with the same, entire reference library as used for FIG. 2 was used to identify a property of the test cell substrate, namely resistance or susceptibility to CTX. The highest degree of matching of spectrometric measurement data with reference datasets selected from the library 301 was determined as the logarithm of the similarity measure (log(score)) of 1.83 with a mass-spectrometric reference dataset of Citrobacter farmeri from the entire reference library, and thus was evaluated as allowing a taxonomic classification of the genus. In the course of the second match result, the property "CTX-resistant" was phenotypically determined for the test cell substrate with the taxonomic classification Citrobacter farmeri in the second preparation. Thus, determining the test cell substrate property by comparing the linear mass spectrum with the reference library resulted in the false-positive determination of the test cell substrate as CTX-resistant Citrobacter farmeri. Such a characterization result can be dismissed as unreliable relatively quickly by someone skilled in the art if, for example, detection of the quantification standard 305 was not reliable, the taxonomic classification was based on a small number of mass peaks that were able to be assigned with high confidence to a peak of the reference dataset in the match result, and/or the number of peaks of the measurement data in the reference dataset used with which the measurement result was compared was small.
Figure 4:
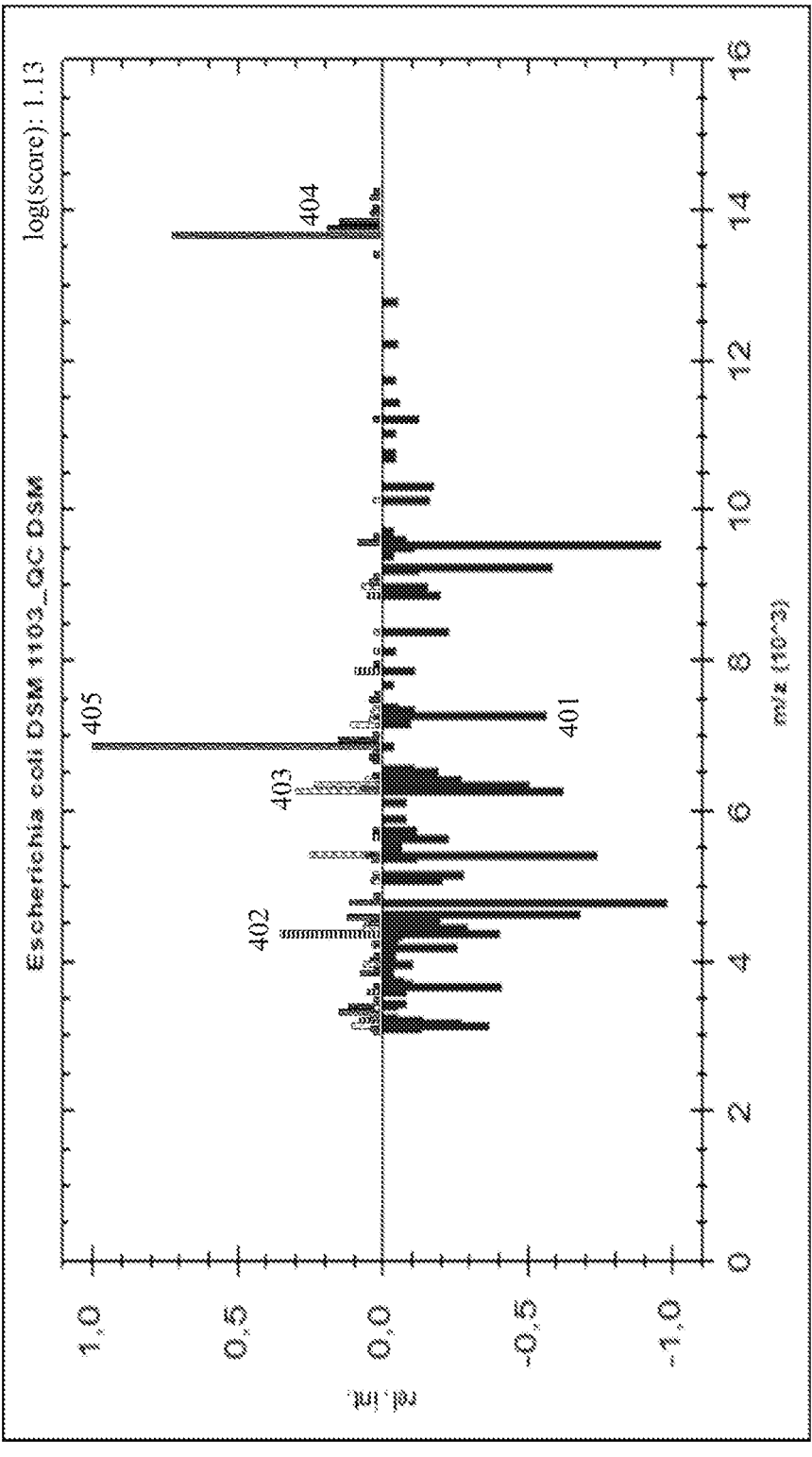
FIG. 4 shows an example of a mass-spectrometric analysis of the second preparation of the same test cell substrate E. coli ((CTX) treatment) as performed for FIG. 3, according to the present invention. Sub-libraries were created for this purpose prior to creating the spectrometric measurement data of the second preparation. A first sub-library comprised the five mass-spectrometric reference datasets from the library with which the measured mass spectrum of the first preparation showed the highest degree of matching and which were evaluated as allowing a taxonomic classification. A second sub-library comprised those reference spectra that, in the first match result for the growth control, had yielded a logarithm of the similarity measure (log(score)) of less than 1.7, i.e., a logarithm of the similarity measure (log(score)) that is typically evaluated as not allowing a taxonomic classification of the species or genus, with the mass-spectrometric measurement results of the first preparation. The comparison of the spectrometric measurement data of the second preparation with the first sub-library was used to determine a property of the test cell substrate, namely resistance or susceptibility to CTX. The highest degree of matching of the spectrometric measurement data with reference datasets selected from the first sub-library 401 was determined as the logarithm of the similarity measure (log(score)) of 1.13 with a mass-spectrometric reference dataset of *E. coli*, the same reference dataset as used in FIG. 2, and thus evaluated as not allowing taxonomic classification of the species or genus. In the course of this second match result, the property "CTX-susceptible" was phenotypically determined for the test cell substrate with the taxonomic classification *E. coli* in the second preparation. Thus, determination of the test cell substrate property by comparing the linear mass spectrum with the first sub-library resulted in the correct specific characterization of the cell substrate as CTX-susceptible *E. coli*. By comparing with the second sub-library, it was possible to exclude the possibility that a different test cell substrate was present in the second preparation than the one inoculated in the first preparation, for example as a result of cell substrate contamination, or that an inhomogeneous test cell substrate was present in the first and second preparations.

The test cell substrate was incubated in nutrient medium, Mueller-Hinton nutrient medium (first preparation—FIG. 2), and the same nutrient medium containing CTX at a concentration of 1 µg/mL (second preparation—FIGS. 3 and 4). The first preparation served as a growth control. The second preparation was used to determine the resistance/susceptibility of the test cell substrate to CTX.

To create the preparations, a large volume (stock suspension) of a cell suspension, here about 12 mL, otherwise regularly 10 to 50 mL, of the test cell substrate was prepared in Mueller-Hinton nutrient medium, a liquid nutrient medium. The concentration of the test cell substrate in the stock suspension was determined densitometrically in order to use an appropriate and equal amount of the test cell substrate for the first and second preparations. A small volume was taken from this stock suspension for the first preparation and transferred to a well of a microtiter plate. Since the first preparation was designed as a growth control, no antibiotic was present in the well. Simultaneously, for a second preparation, the same volume of stock suspension was removed and transferred to another well of the microtiter plate, thereby dissolving the antibiotic CTX, which was present in dried form in the well of the second preparation, for a final concentration of 1 µg/mL. The microtiter plate was then agitated to ensure complete dissolution and homogeneous distribution of the antibiotic in the cavity of the second preparation. Further preparations in the form of a concentration-dilution series for determining of a minimum inhibitory concentration (MIC) of the antibiotic CTX is easy to generate by selectively dissolving the dried CTX in additional wells of the microtiter plate. For example, a CTX concentration of 0.5 µg/mL can be set in the Mueller-Hinton nutrient medium in a third well for another preparation, and a CTX concentration of 2 µg/mL can be set in a fourth well for yet another preparation. Thus, the dilution series can comprise the CTX concentrations 0.5, 1 and 2 µg/mL, while additional dilution steps, e.g., 0.25 or 4 µg/mL can be included. Such a dilution series can also be performed in dilution steps of different sizes of the CTX concentration.

Subsequently, a small volume of 6 µL of the first preparation of the test cell substrate, which was in Mueller-Hinton nutrient medium, was placed on a sample spot of an MBT Bio-target™ sample support. Similarly, for the second preparation, a small volume of 6 µL of the second preparation of the test cell substrate, which was present in 1 µg/mL CTX-containing Mueller-Hinton nutrient medium, was placed on another sample spot of the MBT Biotarget™ sample support. Further inocula of the test cell substrate with other CTX concentrations in the Mueller-Hinton nutrient medium (dilution series of the antibiotic see above) can be applied to further sample points of the sample support, e.g., to spectrometrically determine an MIC of CTX for the test cell substrate. By determining the CTX concentration of the preparation is just enough to still inhibit growth of the test cell substrate, compared to the first preparation, it would be possible to determine the MIC as a property of the second preparation. In the present case, the MIC would be able to be reliably determined at 0.5 µg/mL or 1 µg/mL CTX, if further preparations with 0.5, 1 and 2 µg/mL CTX were applied in the microtiter plate.

The MBT Biotarget™ sample support plate was incubated in an incubation chamber for 4 hours at constant environmental conditions, such as temperature and humidity. In repetitions of the experiment, the incubation time was extended to 6 hours, which increased the biomasses available for measurement generated by the microorganisms in the suspensions. During this time, the cell substrate was able to attach or sediment at the interface between the droplet liquid and the support surface. After the standing time of 4 hours, the residual liquid of the nutrient medium was removed from the sample spot by means of an absorbent tissue that was brought into contact with the droplet on a spot on the support surface from the side, and most of the liquid was simply sucked up. The test cell substrate deposit exposed in this manner was subsequently further prepared and measured in a mass spectrometer, as known in the prior art. For example, peptides/proteins of the cell substrates were extracted and/or the deposited cell substrate was embedded in a MALDI matrix substance, and a quantification standard of the cell substrate sample was added along with the matrix. In the experiments performed for FIGS. 2 through 4A, a quantification standard was added to the test cell substrate sample. The peak measured for this quantification standard far outperformed all other mass signals. However, as an extrinsic peak, it was not used for taxonomic classification, and is consequently shown as a dotted bar in the positive range of values (205, 305, 405).

The test cell substrates from the first and second preparations were then subjected to mass-spectrometric analysis using the MALDI Biotyper® system. First, the first preparation of the test cell substrate used as a growth control was measured using mass spectrometry, and a taxonomic classification of the test cell substrate was performed by comparing the obtained linear mass spectra with the reference mass spectra of the reference library of the MALDI Biotyper® system.

Within the obtained first match result, the reference mass spectrum with the highest degree of matching (best match) to the measured spectrum was used for taxonomic classification. FIG. 2 shows an example of such a best match for the first preparation. The measured mass spectrum had a logarithm of the similarity measure (log(score)) of 2.34 with a reference spectrum of *E. coli* DSM 1103. In addition to this best match, i.e., the mass-spectrometric *E. coli* reference dataset that was most similar to the measured spectrum, other similar reference datasets, such as those allowing taxonomic classification with respect to the genus *Escherichia* sp., and non-similar mass-spectrometric reference datasets were identified within the first match result throughout the library. The non-similar mass-spectrometric reference datasets did not allow taxonomic classification of the species or genus of the cell substrate and belonged, for example, to other genera such as *Citrobacter* sp. The reference datasets from the library which were listed in the first match result were able to be evaluated and classified as allowing a taxonomic classification or not allowing a taxonomic classification of the species or genus based on the logarithm of the similarity measure. The comparison of the obtained mass spectrum of the first preparation with the reference library assigned the measured linear mass spectrum to the species *E. coli* as the test cell substrate under investigation, based on the log(score)s of 2.34, as the value was above the log(score) 2.0, as specified for the MALDI Biotyper® system.

Furthermore, the property of susceptibility or resistance (susceptibility/resistance) to CTX was determined using a prior art method and the method disclosed herein for the second preparation of the test cell substrate. The second preparation (CTX treatment) was measured using mass spectrometry and the linear mass spectrum obtained was compared with the entire reference library (FIG. 3). A small number of mass-spectrometric peaks were measured. Based on this small number of peaks, the comparison was performed with the entire MALDI Biotyper® library. In FIG. 3, a linear mass spectrum, as part of a match result, of a mass-spectrometric measurement is shown, and a log(score) of 1.83 is given as an evaluation of the degree of matching with a reference spectrum of *Citrobacter farmeri* (best match). The reference peaks 301 used to determine the degree of matching are shown as solid bars in the negative range of values. Those mass peaks that were able to be assigned with high reliability to a peak of the reference dataset in the match result are shown as horizontally hatched bars in the positive range of values 302, while those that could still be assigned with sufficient reliability to a peak of the reference dataset, are shown as cross-hatched bars in the positive value range 303, and those peaks that could not be sufficiently assigned to a peak of the reference dataset are shown as dotted bars in the positive value range 304. The relative quantification standard that was used 305 was measured but not used for taxonomic classification.

The taxonomic classification was based on a log(score) of 1.83, which is evaluated as allowing a reliable determination of the genus. Therefore, the determination of the property of resistance/susceptibility in culturability, i.e., resistance to CTX, was determined even though the test cell substrate had actually been sensitive (susceptible) to CTX. Reliable taxonomic classification plays an important role in phenotypic determination of resistance or susceptibility to an antimicrobial agent such as an antibiotic. Thus, the taxonomic classification of the test cell substrate as *Citrabacter* sp. contributed to the determination of the test cell substrate as resistant.

As a result, it is possible that (false-positive) evaluation as allowing a taxonomic classification to a genus different from the taxonomic classification of the growth control, as in the present case a taxonomic classification to the genus *Citrobacter* sp., and a determination of the property of resistance to CTX for the cell substrate occurred. In this experimental approach, a log(score) that allowed taxonomic classification of the species or a log(score) that allowed taxonomic classification of the genus, as repeat experiments showed and is represented in FIG. 3, can but does not have to be determined. Thus, it may occur that, for determining the resistance property of the second preparation, despite a low number of measured mass peaks in the second measurement result, or despite the determination of the match result of the generated second measurement data with the entire reference library using a small number of measured peaks, which could be assigned with high 302 or sufficient 303 reliability to a reference peak in the reference spectra used 301, a match result allowing a taxonomic classification was determined in the obtained second match result and the property CTX-resistant was determined. These false-positive characterization results can be discarded by the skilled user after checking because, for example, for the phenotypic determination of the property CTX susceptibility or resistance by means of the measured mass spectra of the second preparation, the number of measured peaks was small and/or the number of measured peaks that could be assigned with high 302 or sufficient 303 reliability to a reference peak in the reference spectra used 301 was small, which was insufficient for a reliable taxonomic determination and/or a determination of the property of the test cell substrate was insufficient. Low biomass of the cell substrate in the second preparation after the incubation period had elapsed contributed to the false-positive assignment CTX-resistant *Citrobacter* sp.

In a mass-spectrometric analysis of the mass-spectrometric measurement data from the second preparation for FIG. 4, which was performed in parallel with the characterization of the test cell substrate in the second preparation for FIG. 3, sub-libraries were created prior to the creation of the spectrometric measurement data from the second preparation. A first sub-library was used to provide a second match result based on the measurement results of the second preparation. This first sub-library comprised five mass-spectrometric reference datasets from the library that were most similar to the measured mass spectrum from the first preparation and were evaluated as allowing a taxonomic classification. In the selection from the library, the five reference datasets that had the highest similarity measures ("score") or their logarithm (log(score)) were selected. Such reference datasets that belonged to genera other than the genus determined for the test cell substrate based on the match result of the measurement data of the first preparation, such as *Citrobacter* sp., were excluded in the first sub-library because they had not allowed taxonomic classification in the first match result. In repetitions of the analysis, the number of mass-spectrometric reference datasets included in the second sub-library was reduced to the three reference datasets with the highest degree of matching, while maintaining the improved effect.

The comparison of the spectrometric measurement data from the second preparation with the first sub-library was used to identify a property of the test cell substrate, namely resistance or susceptibility to CTX. Those mass peaks that were able to be assigned with high reliability to a peak of the reference dataset in the match result are shown as horizontally hatched bars in the positive range of values 402, while those that could still be assigned with sufficient reliability to a peak of the reference dataset, are shown as cross-hatched bars in the positive value range 403, and those peaks that could not be sufficiently assigned to a peak of the reference dataset are shown as dotted bars in the positive value range 404. The relative quantification standard that was used 405 was measured but not used for taxonomic classification. In the second match result from the comparison of the mass-spectrometric data of the second preparation with the first sub-library, the log(score) was set to 1.13 (i.e. below 1.7) with a mass-spectrometric reference spectrum 401, shown as solid bars in the negative value range, of *E. coli*, the same reference dataset used in FIG. 2, and thus the property of the cell substrate as CTX-susceptible was determined (FIG. 4). This demonstrated that the *E. coli* cell substrate had not survived in CTX-containing Mueller-Hinton nutrient medium according to the taxonomic classification of the first preparation. The cell substrate was thus correctly determined as CTX-susceptible *E. coli*. The specificity of the taxonomic classification and the determination of the CTX-resistance property, even with insufficient measurement data, was thus improved and manual checking of the match results of the second preparation was rendered superfluous or at least its necessity was greatly reduced. As a result, the specificity of the characterization of the test cell substrate has been improved and the prospects for automating the characterization of the test cell substrate has been improved, since the need for manual checking of the determination of the property of the test cell substrate can be eliminated, or at least greatly reduced.

A second sub-library was created in addition to the first sub-library. The second sub-library comprised those reference spectra that had yielded a logarithm of the similarity measure (log(score)) of less than 1.7 for growth control in the first match result, i.e., typically evaluated as not allowing taxonomic classification of the species or genus, with the mass-spectrometric measurement results of the first preparation. In particular, the five mass-spectrometric reference datasets of the first sub-library were not included in the second sub-library. The second sub-library comprised those reference datasets which were evaluated in the first match result as not allowing a taxonomic classification of the species or genus. The spectrometric measurement results of the second preparation were compared with the second sub-library in addition to the first sub-library. This third comparison was used for quality assurance of the second match result in the form of a negative control. A result allowing a taxonomic classification should not be achieved in this third comparison, or should even be excluded. In the experiment performed, no logarithm of the similarity measure allowing a taxonomic classification could be determined for this third match result. Thus, it was ruled out that a different test cell substrate than the one originally inoculated was present as a result of cell substrate contamination or an inhomogeneous test cell substrate in the second preparation.

Definitions

Unless otherwise defined, the formulations used comprise the general and technical understanding of the person skilled in the art. In particular, the following formulations describe the technical understanding of the person skilled in the art. Examples are not intended to limit the invention, but to explain the understanding of the person skilled in the art.

Where "one," "a," or "the" is used herein, it may refer to one or more. For example, "a cell" may describe a single cell or a multitude of cells.

Where "and/or" is used herein, it refers to and comprises each and every possible combination of one or more associated listed items, as well as the absence of combinations when linked as an alternative, i.e., as "or".

Furthermore, terms such as "approximately," "about," or the like, when referring to a measurable quantity such as the amount of an agent, such as a growth-influencing factor mean that variations of that quantity of ±20%, ±10%, ±5%, ±1%, ±0.5%, or even ±0.1%. are included.

The terms "cell substrate" or "test cell substrates" as used in this application describe a cellular sample that is to be characterized using spectrometric measurements and comparing with libraries and/or sub-libraries. The term describes cellular samples that can be cultured, multiplied and/or handled in the laboratory. The term comprises prokaryotic and/or eukaryotic cells. Moreover, the term comprises cellular samples that have an intracellular and/or extracellular lifestyle. The term may describe plant, animal, and/or fungal cells. Additionally, the term comprises unicellular and/or multicellular and/or motile, e.g., flagellated, and/or non-motile cellular substrates. A cell substrate can be a cell substrate isolated from an organism. Examples of isolated cell substrates comprise tumor cells, cells affected by a pathogen, or certain cell populations, such as macrophages or T cells. For example, tumor cells can be isolated from a lymphoma, leukemia, or solid tumor. Cell substrates can be isolated using a variety of methods. Examples are known to the person skilled in the art and comprise flow cytometric methods or bead-based methods.

In one embodiment, the term "cell substrate" describes cellular samples that have an intracellular lifestyle, particularly intracellular microbes, such as *Mycobacterium avium, Mycobacterium intracellulare* or *Listeria monocytogenes.*

In an exemplary embodiment, the term "cell substrate" describes "microorganisms" or "microbes". The term "microorganisms" or "microbes" comprises microscopic organisms consisting of one or a few cells. Microbes comprises gram-negative and gram-positive bacteria, yeasts, molds, parasites, and mollicutes. Examples of gram-negative bacteria comprise bacteria of the following genera: *Pseudomonas, Escherichia, Salmonella. Shigella, Enterobacter, Klebsiella, Serratia, Proteus, Campylobacter, Haemophilus, Morganella, Vibrio, Yersinia, Acinetobacter, Stenotrophomonas, Brevundimonas, Ralstonia, Achromobacter, Fusobacterium, Prevotella, Branhamella, Neisseria, Burkholderia, Citrobacter, Hafnia, Edwardsiella, Aeromonas, Moraxella, Brucella, Pasteurella, Providencia,* and *Legionella.* Examples of gram-positive bacteria comprise bacteria of the following genera: *Enterococcus, Streptococcus, Staphylococcus, Bacillus, Paenibacillus, Lactobacillus, Listeria, Peptostreptococcus, Propionibacterium, Clostridium, Bacteroides, Gardnerella, Kocuria, Lactococcus, Leuconostoc, Micrococcus, Mycobacteria* and *Comybacteria.* Examples of fungi comprise yeasts and molds of the following genera: *Candida, Cryptococcus, Nocardia, Penicillium, Alternaria, Rhodotorula, Aspergillus, Fusarium, Saccharomyces* and *Trichosporon.* Examples of parasites comprise parasites of the following genera: *Trypanosoma, Babesia, Leishmania, Plasmodium, Wucheria, Brugia, Onchocerca* and *Naegleria.* Examples of mollicutes comprise mollicutes of the following genera: *Mycoplasma* and *Ureaplasma.*

The singular "microbe" also means, as is usual in general parlance, the species of microbe as well as an individual microbial cell. The plural "microbes" means the microbial cells under analysis. Microorganisms are found in the taxonomic domains of Bacteria, Archaea, and Eukaryota, and particularly comprise bacteria, archea, fungi, microalgae, and protozoa.

In an exemplary embodiment, the terms "cell substrate" or "test cell substrate" describe microorganisms, such as bacteria, particularly gram-negative bacteria, and most particularly bacteria of the family Enterobacteriaceae.

In another embodiment, the terms "cell substrate" or "test cell substrate" describe isolated tumor cells, particularly isolated malignant tumor cells, such as isolated malignant tumor cells of a solid tumor.

The term "preparation" within the meaning of this application describes a work procedure by which the initially available biomass of the test cell substrate under investigation is processed and prepared for a spectrometric measurement, in particular a mass-spectrometric measurement. A preparation may include a multiplication step of the test cell substrate to increase the available biomass and thus to enhance the detectable spectral signals compared to ubiquitous background or noise in spectrometric measurement data. Various forms of preparation for preparing cell substrates for spectrometric measurements are known to the person skilled in the art. A preparation may comprise the incubation of the cell substrate.

The term "incubation" as used in this application comprises all forms of incubating, i.e., growing or culturing, cell substrates. The cell substrate may undergo a multiplication step. Incubation is enabled by creating and maintaining conditions that ensure life, survival and/or growth of the test cell substrate. Nutrient or culture media, or media for short, are used to incubate the test cell substrates. Typically, a nutrient medium contains a major portion of water, an energy source usable by the test cell substrate, and nutrients or substrates required by the test cell substrate, but a nutrient medium may have other compositions. Furthermore, a nutrient medium may contain salts that can supply important ions to the organism, dyes or their precursors, gelling agents for solidifying the nutrient medium, such as agar, gellan and/or silica gel, growth-influencing factors, indicators and/or buffer substances. If the test cell substrate is eukaryotic, i.e., animal or plant cells, the incubation is also referred to as a cell culture. The term "incubation" comprises incubation on solid, gelled, semi-solid and/or in liquid media, where media may be placed in different vessels or on different supports, such as a MALDI sample support, e.g., an AnchorChip™ (Bruker) or an MBT Biotarget™ (Bruker). For incubating animal cells, mainly liquid nutrient media are used, and for plant cells mainly liquid and solid nutrient media. Typically, the test cell substrate is incubated in a medium with the same composition for the first and the second and/or the further preparations. However, the composition of the media for the first and second and/or further preparations can be different if the different ingredient(s) is/are intended as a growth-influencing factor. Typically, cell substrates are incubated on or in a medium in a heating cabinet, heating room or incubator. Typical incubation periods are 2 h, 4 h, 6 h, 8 h, 12 h, 24 h, 36 h or 48 h with the exemplary incubation periods being 2 h to 8 h, ideally 4 h to 6 h. If the cell substrate undergoes a multiplication step, the person skilled in the art knows the typical generation times, i.e., the time period in which the number of individuals in a population doubles, e.g., about 20 minutes for *E. coli*, about 30 minutes for *S. aureus* or *Salmonella*, or about 18 h for *Mycobacterium tuberculosis.*

For the purposes of this application, a "taxonomic classification" of a "cell substrate" and, particularly a microorganism, comprises the classification of the test cell substrate at a taxonomic level down to genus (genus), species (species), subspecies (subspecies), and/or variety or serotype. In one embodiment, the term comprises the taxonomic classification of the test cell substrate at the genus or species level.

The term "growth-influencing factor" as used in this application comprises any substance, treatment, and/or environmental condition, the addition or modification of which alters the growth conditions for the test cell substrate. Growth-influencing factors can have a positive or a negative effect on the vitality and/or viability of the test cell substrate.

Examples of growth-influencing factors that can have a positive effect on the vitality and/or viability of the test cell substrate include growth factors, e.g., hematopoietic growth factors such as erythropoietin or granulocyte colony-stimulating factor (G-CSF), macrophage colony-stimulating factor (M-CSF), granulocyte macrophage colony-stimulating factor (GM-CSF), or for bacteria, by the supply of certain carbon, nitrogen, and sulfur sources or the presence of certain electromagnetic radiation (light) in (facultatively) phototrophic bacteria.

Examples of growth-influencing factors that can have a negative effect on the vitality and/or viability of the test cell substrate include bioactive substances, in particular any chemical substance (element, compound, or mixture) that has a direct toxic effect, e.g., bactericidal or cytotoxic, or growth inhibitory, i.e., bacteriostatic or cytostatic, on the test cell substrate and negatively affects its vitality and/or growth compared with a growth control to which this chemical substance is not added. The solid, gelled, semi-solid and liquid media in or on which an incubation of the test cell substrate takes place, in particular an incubation for a first preparation, are not growth-influencing factors in the sense of this application, because these are only the created conditions that make an incubation possible. However, if these conditions are not identical for the incubation of the test cell substrate for a first preparation and a subsequent preparation, in particular a second preparation, then the difference in the created conditions can be a growth-influencing factor. Examples of growth-influencing factors include chemical agents and antimicrobials such as antibiotics, antifungals or cytostatics.

A growth-influencing factor may also be the combination of more than one factor, such as a combination of two different antibiotics. Moreover, the term "growth-influencing factor" also comprises changes in culture and incubation conditions, such as changes in the composition of a nutrient medium used, the period of incubation, and environmental conditions such as temperature, composition of ambient air, and humidity during incubation. Furthermore, the term "growth-influencing factor" also comprises physical treatments of the cell substrate, such as irradiation of the cell substrate with a light of a certain wavelength or intensity. The growth-influencing factor may already be present in the nutrient medium prior to the addition of a cell substrate inoculum, for example in the form of a solution or powder, or in a lyophilized form. The growth-influencing factor may also be present in a vessel, such as the well of a microtiter plate, in the form of a powder, or in a dried or lyophilized form, and only dissolved and adjusted to the desired concentration by the addition of a certain volume of the cell substrate inoculum. Alternatively, the growth-influencing factor(s) may be added to the nutrient medium after the cell substrate has been added. In an exemplary embodiment, the growth-influencing factor has a negative effect on the vitality and/or viability of the test cell substrate.

In an exemplary embodiment, the growth-influencing factor is an antibiotic selected from cephalosporins, gyrase inhibitors or fluoroquinolones, macrolides, clindamycin, penicillins, sulfonamides, tetracyclines, carbapenems, and/or trimethoprim.

In another embodiment, the growth-influencing factor is an antibiotic selected from piperacillin/tazobactam (PIT), Cefotaxime (CTX), Ertapenem (ERT), Ceftazidime/Avibactam (CAA), Meropenem (MER), Ciproflaxicin (CIP), Ceftazidime (CAZ), Amikacin (AMK) and/or Gentamicin (GEN). A concentration of such an antibiotic might, for example, be selected from 0.01 µg/mL-200 µg/mL, 0.1 µg/mL-20 µg/mL, 0.25 µg/mL-18 µg/mL, 0.5 µg/mL-15 µg/mL, 1 µg/mL-10 µg/mL, 1 µg/mL-8 µg/mL, 1 µg/mL-6 µg/mL or 1 µg/mL-4 µg/mL. In one particular embodiment, the growth-influencing factor is selected as antibiotic PIT at a concentration of 4 µg/mL, 6 µg/mL or 8 µg/mL. In another alternative embodiment, the growth-influencing factor is selected as antibiotic CTX at a concentration of 1 µg/mL, 2 µg/mL or 4 µg/mL. In yet another embodiment, the growth-influencing factor is selected as antibiotic ERT at a concentration of 0.5 µg/mL or 1 µg/mL. In another embodiment, the growth-influencing factor is selected as antibiotic CAA at a concentration of 4 µg/mL, 6 µg/mL or 8 µg/mL. In still another embodiment, the growth-influencing factor is selected as antibiotic MER at a concentration of 2 µg/mL, 4 µg/mL or 8 µg/mL. In another embodiment, the growth-influencing factor is selected as antibiotic CIP at a concentration of 0.125 µg/mL, 0.25 µg/mL or 0.5 µg/mL. In another embodiment, the growth-influencing factor is selected as antibiotic CAZ at a concentration of 1 µg/mL, 2 µg/mL or 4 µg/mL. In another embodiment, the growth-influencing factor is selected as antibiotic AMK at a concentration of 4 µg/mL or 8 µg/mL. In another embodiment, the growth-influencing factor is selected as antibiotic GEN at a concentration of 1 µg/mL or 2 µg/mL.

In another embodiment, the cell substrate is a microbe and the growth-influencing factor, an antimicrobial agent, such as an antibiotic, more specifically, the microbe is a bacterium and the antimicrobial agent is an antibiotic selected from piperacillin/tazobactam (PIT), cefotaxime (CTX), ertapenem (ERT), ceftazidime/avibactam (CAA), meropenem (MER), ciproflaxicin (CIP), ceftazidime (CAZ), amikacin (AMK) and/or gentamicin (GEN), and in a particular embodiment, the microbe is a bacterium of the family Enterobacteriaceae and the antibiotic is selected from PIT, CTX, ERT, CAA, MER, CIP, CAZ, AMK and/or GEN, and the concentration of the antibiotic is selected from 0.01 µg/mL-200 µg/mL, 0.1 µg/mL-20 µg/mL, 0.25 µg/mL-18 µg/mL, 0.5 µg/mL-15 µg/mL, 1 µg/mL-10 µg/mL, 1 µg/mL-8 µg/mL, 1 µg/mL-6 µg/mL, or 1 µg/mL-4 µg/mL.

In yet another embodiment, the cell substrate or test cell substrate is a microbe and the growth-influencing factor, an antimicrobial agent, such as an antibiotic or antifungal, more particularly, the microbe is a bacterium and the anti-microbial agent is an antibiotic selected from piperacillin/tazobactam (PIT), cefotaxime (CTX), ertapenem (ERT), ceftazidime/avibactam (CAA), meropenem (MER), ciproflaxicin (CIP), ceftazidime (CAZ), amikacin (AMK) and/or gentamicin (GEN). In certain exemplary embodiments, the microbe is a bacterium of the family of Enterobacteriaceae and the antibiotic is selected from PIT, CTX, ERT, CAA, MER, CIP, CAZ, AMK and/or GEN, and the first and second preparations comprise incubation of the microbes, wherein the incubation in at least one preparation comprises a multiplication step, such as an incubation with an incubation period of 4 h to 6 h, wherein the incubation comprises a multiplication step in the first preparation.

In another embodiment, the cell substrate or test cell substrate is a microbe and the growth-influencing factor, an antimicrobial agent such as an antibiotic or antifungal. For example, the microbe may be a bacterium and the antimicrobial agent is an antibiotic selected from piperacillin/tazobactam (PIT), cefotaxime (CTX), ertapenem (ERT), Ceftazidime/Avibactam (CAA), Meropenem (MER), Ciproflaxicin (CIP), Ceftazidime (CAZ), Amikacin (AMK) and/or Gentamicin (GEN), particularly the microbe is a bacterium of the Enterobacteriaceae family and the antibiotic is selected from PIT, CTX, ERT, CAA, MER, CIP, CAZ, AMK, and/or GEN, and the concentration of the antibiotic is selected from 0.01 µg/mL-200 µg/mL, 0.1 µg/mL-20 µg/mL, 0.25 µg/mL-18 µg/mL, 0.5 µg/mL-15 µg/mL, 1 µg/mL-10 µg/mL, 1 µg/mL-8 µg/mL, 1 µg/mL-6 µg/mL, or 1 µg/mL-4 µg/mL, and the first and second preparation comprises incubation of the microbes, wherein the incubation in at least one preparation comprises a multiplication step, such as an incubation lasting 4 h to 6 h, wherein the incubation comprises a multiplication step in the first preparation.

The terms "mass spectrum" or "mass-spectrometric analysis" comprise the raw mass spectrometric data through to a processed peak list containing only the positions and intensities of mass signals. A mass spectrum here can consist of a large number of intensity values in a continuous mass range, but also the intensity values of several separate mass ranges. The mass spectrum can undergo signal processing before the quantity of microbes is determined. This processing can, for example, comprise correction (subtraction) of the base line, smoothing of mass signals, elimination of noise signals and/or selection of mass signals above a specified noise value. The mass spectrum can be a sum mass spectrum in which single mass spectra have been added. Exemplary ranges of charge-related mass (alternatively called mass-to-charge ratio) are between m/z 2000 and m/z 20000, often between m/z 3000 and m/z 15000, especially when the test cell substrate is a microorganism.

The term "densitometric measurement" or "densitometry" as used in this application comprises all methods of direct or indirect quantitative measurement for the determination of cell substrate concentration. Densitometry thus comprises indirect measurement methods, such as photometric turbidity measurements or optical density measurements (apparent optical density OD) based on light scattering using a photometer or spectrometer. Typically, optical density measurement is performed in a wavelength range of the light spectrum from 560 to 600 nanometers, i.e., a wavelength range in which no pigments of the cells absorb. OD can be measured as density or absorbance for microorganisms in a spectrophotometer at 600 nanometers or in a filter photometer at 578 nanometers. Other methods for quantifying the biomass of a preparation include direct methods such as determining the dry weight, cell protein, or total nitrogen of the preparation.

The invention has been described above with reference to several specific example embodiments. However, it is understood that various aspects or details of the described embodiments may be changed without deviating from the scope of the invention. Furthermore, the features and measures disclosed in connection with various embodiments may be combined as desired, if this appears practicable to a person skilled in the art. Moreover, the above description serves only as an illustration of the invention and not as a limitation of the scope of protection, which is exclusively defined by the appended claims, taking into account any equivalents which may exist.

The invention claimed is:

1. A method for spectrometrically characterizing a test cell substrate, comprising:
   a) providing a library comprising a multitude of reference data sets, with each reference data set containing data that allows a taxonomic classification of a cell substrate;
   b) obtaining first spectrometric measurement data from the test cell substrate after a first preparation;
   c) comparing the first spectrometric measurement data or data derived therefrom with the library to determine a first match result, wherein a match result contains a list of reference data sets and their degree of matching with spectrometric measurement data of a cell substrate or data derived therefrom;
   d) creating a sub-library comprising reference data sets from the library for which the first match result is evaluated as allowing a taxonomic classification of the test cell substrate;
   e) obtaining second spectrometric measurement data from the test cell substrate after at least a second preparation under conditions that are not identical to the conditions of the first preparation;
   f) comparing the second spectrometric measurement data or data derived therefrom with the sub-library to determine a second match result; and
   g) determining a property of the test cell substrate using the second match result.

2. The method according to claim 1, wherein the taxonomic classification comprises assignment to the test cell substrate of a taxon selected from the group: genus; species; subspecies; and variety or serotype.

3. The method according claim 1, wherein the test cell substrate comprises bacteria of the family Enterobacteriaceae.

4. The method according to claim 1, wherein each of the first preparation and second preparation include a multiplication step of the test cell substrate.

5. The method according to claim 1, wherein the second preparation is carried out in the presence of a growth-influencing factor.

6. The method according to claim 1, wherein the first preparation is carried out as a growth control without using a growth-influencing factor.

7. The method according to claim 1, wherein a reference data set comprises a spectrum or a data n-tuple derived from a spectrum.

8. The method according to claim 1, wherein the property to be determined comprises a susceptibility and/or resistance of the test cell substrate to a growth-influencing factor.

9. The method according to claim 8, wherein the property to be determined comprises a minimum inhibitory concentration (MIC) of the growth-influencing factor for the test cell substrate.

10. The method according to claim 1, wherein reference data sets for which the first match result is evaluated as not allowing a taxonomic classification of the test cell substrate are excluded from the creation of the sub-library.

11. The method according to claim 1, wherein the sub-library is a first sub-library, and wherein a second sub-library is created that comprises reference data sets from the library for which the first match result is evaluated as not allowing a taxonomic classification of the test cell substrate, and wherein the second spectrometric measurement data or data derived therefrom is compared with the second sub-library in order to determine a third match result, and a property of the test cell substrate is determined using the third match result.

12. The method according to claim 1, wherein the obtaining of the first and/or the second spectrometric measurement data from the test cell substrate comprises mass spectrometric analysis.

13. The method according to claim 1, further comprising further preparations of the test cell substrate under conditions that are not identical to the conditions of the first preparation or second preparation or with each other.

14. The method according to claim 1, wherein the first preparation and/or the second preparation is carried out directly on a sample support which serves as a substrate for obtaining spectrometric measurement data.

15. The method according to claim 1, wherein:
   a) the test cell substrate comprises bacteria of the family Enterobacteriaceae;
   b) the first preparation and second preparation each comprise a multiplication step,
   c) the second preparation is carried out in the presence of a growth-influencing factor;
   d) the first preparation is carried out as a growth control without the use of a growth-influencing factor;
   e) the taxonomic classification comprises assignment to the test cell substrate of a taxon selected from the group consisting of: genus; species; subspecies; and variety or serotype;
   f) at least one of the reference data sets comprises a spectrum or a data n-tuple derived from a spectrum;

g) the growth-influencing factor is an antimicrobial agent, and the property of the test cell substrate is a susceptibility or resistance of the test cell substrate to the antimicrobial agent;

h) reference data sets for which the first match result is evaluated as not allowing a taxonomic classification of the test cell substrate are excluded in the provision or creation of the sub-library;

i) the sub-library is a first sub-library, and wherein a second sub-library is created that comprises the reference data sets from the library for which the first match result is evaluated as not allowing a taxonomic classification of the test cell substrate, and wherein the second spectrometric measurement data or data derived therefrom is compared with the second sub-library to determine a third match result;

j) the third match result is evaluated as not allowing taxonomic classification of the test cell substrate; and k) the obtaining of first and/or second spectrometric measurement data from the test cell substrate comprises a mass spectrometric analysis.

* * * * *